(12) United States Patent
Ding et al.

(10) Patent No.: US 11,892,441 B2
(45) Date of Patent: Feb. 6, 2024

(54) TRANSBOUNDARY-AREA WATER-BODY MONITORING AND EARLY WARNING SYSTEM

(71) Applicants: Nanjing Institute of Environmental Sciences, Ministry of Ecology and Environment, Nanjing (CN); Jiangsu JHS Environment Technologis Co., Ltd., Nanjing (CN)

(72) Inventors: Chengcheng Ding, Nanjing (CN); Yibin Cui, Nanjing (CN); Jianhua Dai, Nanjing (CN); Nan Shen, Nanjing (CN); Shudong Wang, Nanjing (CN)

(73) Assignees: NANJING INSTITUTE OF ENVIRONMENTAL SCIENCES, MINISTRY OF ECOLOGY AND ENVIRONMENT, Nanjing (CN); JIANGSU JHS ENVIRONMENT TECHNOLOGIES CO., LTD., Nanjing (CN)

( * ) Notice: Subject to any disclaimer, the term of this patent is extended or adjusted under 35 U.S.C. 154(b) by 267 days.

(21) Appl. No.: 17/400,958

(22) Filed: Aug. 12, 2021

(65) Prior Publication Data
US 2022/0065838 A1  Mar. 3, 2022

(30) Foreign Application Priority Data
Aug. 28, 2020 (CN) .......................... 202010886659.7

(51) Int. Cl.
G01N 33/18 (2006.01)
(52) U.S. Cl.
CPC .................................. G01N 33/18 (2013.01)

(58) Field of Classification Search
CPC .......... G01N 33/18; F16J 15/46; G11B 33/14; G11B 33/1466; E21D 11/38;
(Continued)

(56) References Cited

U.S. PATENT DOCUMENTS 3,913,384 A * 10/1975 Furuya ................... G01N 33/18
73/19.1
4,448,425 A * 5/1984 von Bergen ......... B63H 23/321
277/346

(Continued)

FOREIGN PATENT DOCUMENTS

CN 110005810 A * 7/2019

*Primary Examiner* — Son T Le
*Assistant Examiner* — Matthew W. Baca
(74) *Attorney, Agent, or Firm* — Troutman Pepper Hamilton Sanders LLP (Rochester)

(57) ABSTRACT

A transboundary-area water-body monitoring and early warning system includes a monitoring device placed in water body to monitor the water body. The monitoring device comprises a housing body. A control mechanism, a communication mechanism, a sensor and a power box are arranged within the housing body. Power ends of the control mechanism, of the sensor, and of the communication mechanism are electrically connected to an output end of the power box. Control terminals of the communication mechanism and of the sensor are electrically connected to a control terminal of the control mechanism. The control mechanism is configured to receive a signal sent by the sensor, and send the signal from the sensor to a background computer through the communication mechanism. The housing body comprises a lower housing and an upper housing. The lower housing is sealably connected to the upper housing.

8 Claims, 3 Drawing Sheets

(58) Field of Classification Search
CPC .............. E21D 11/385; G03B 2215/00; G03B 2215/0517; G03B 2215/0542
See application file for complete search history.

(56) References Cited

U.S. PATENT DOCUMENTS

| | | | |
|---|---|---|---|
| 9,536,572 B2 * | 1/2017 | Lapp | G11B 33/1486 |
| 2012/0025679 A1 * | 2/2012 | Roering | E06B 7/2318 |
| | | | 49/303 |
| 2019/0072533 A1 * | 3/2019 | Behari | G01N 33/18 |
| 2023/0184576 A1 * | 6/2023 | Harrison | G05D 9/12 |
| | | | 73/292 |

* cited by examiner

TRANSBOUNDARY-AREA WATER-BODY MONITORING AND EARLY WARNING SYSTEM

This application claims the benefit of Chinese Patent Application Serial No. 202010886659.7, filed Aug. 28, 2020, which is hereby incorporated by reference in its entirety.

FIELD

The present disclosure relates to the technical field of water body monitoring technology, and in particular to a transboundary-area water-body monitoring and early warning system.

BACKGROUND

With continuous development of living standards, people have increasing requirements for surrounding environment. However, due to an increase in population density, self-purification ability of natural environment has been unable to satisfy purification of water bodies, such as artificial rivers and artificial lakes in cities. In the prior art, there are mainly human inspections. Different sampling tests are performed on water bodies in various environments based on experience and judgement of inspectors, a report of pollution of the water bodies is made based on sampling results, and then the water bodies are treated. The above mentioned monitoring method for the water bodies depends mainly on the experience of the inspectors. In a practical application, when a problem is found, the water bodies have already been polluted in a large area.

Therefore, it is necessary to provide a device which can monitor water bodies in real time, making up for the shortcomings of human inspections in the prior art, and improving the response to water pollution. Existing water body monitoring and early warning systems in transboundary area are generally achieved by a water body monitoring device. For a traditional water body monitoring device, a sensor is generally directly sealed within a housing placed into the water body to monitor data of the water body. However, only sealant is generally used in a sealing mechanism of the housing, which is very simple. Water can soak through the housing when the housing is in water for a long time. Once electrical components in the housing are immersed in water, it is easy for the electrical components to be short-circuited and damaged.

SUMMARY

An object of the present disclosure is to provide a transboundary-area water-body monitoring and early warning system with a simple structure and a reasonable design, in order to solve the problems mentioned above.

The present disclosure achieves the above object through the following technical solutions.

It is provided a transboundary-area water-body monitoring and early warning system, including a monitoring device placed in water body to monitor the water body. The monitoring device includes a housing body in which a control mechanism, a communication mechanism, a sensor and a power box are arranged. Power ends of the control mechanism, the sensor, and the communication mechanism are electrically connected to an output end of the power box. Control ends of the communication mechanism and the sensor are electrically connected to a control end of the control mechanism. The control mechanism is configured to receive a signal sent by the sensor, and send the signal from the sensor to a background computer through the communication mechanism. The housing body includes a lower housing and an upper housing which are hermetically connected and define an electric installation cavity therebetween. The control mechanism, the communication mechanism, the sensor and the power box are installed within the electric installation cavity. A monitoring probe is installed vertically in a middle of the upper housing and is connected with the sensor. Sealing grooves are provided in an upper surface of the lower housing and a lower surface of the upper housing, at positions close to outer edges of the lower housing and the upper housing, respectively. When the upper housing and the lower housing are assembled, the sealing grooves are arranged facing each other and a sealing water bladder is arranged within the sealing grooves. The housing body is provided with a water circulation mechanism, which includes a water inlet end, a water outlet end and an external water connection end. The water inlet end and the water outlet end of the water circulation mechanism are connected to the sealing water bladder. The external water connection end is communicated with outside. The control end of the control mechanism is connected to a control end of the water circulation mechanism. The control mechanism is configured to control the water circulation mechanism to fill the sealing water bladder with liquid, the sealing water bladder is expanded so as to come into close contact with groove walls of the sealing grooves.

As a development of the present disclosure, the water circulation mechanism comprises a water pump unit and three groups of electromagnetic valves; the three groups of three electromagnetic valves are respectively arranged at the water inlet end, the water outlet end, and the external water connection end of the water circulation mechanism. In an initial state, the electromagnetic valves of the water circulation mechanism at the external water connection end and the water inlet end are first switched on, and water in the water body is injected into the sealing water bladder, so that the sealing water bladder is expanded to come into close contact with the groove walls of the sealing grooves.

As a development of the present disclosure, the water circulation mechanism comprises a water tank, the external water connection end is located on an outer surface of the water tank, and a filter is fixedly connected to the outer surface of the water tank.

As a development of the present disclosure, an inner temperature sensor is fixedly connected to an interior of the housing body. An output end of the inner temperature sensor is electrically connected to an input end of the control mechanism. When a temperature value sensed by the inner temperature sensor is greater than a predetermined value, the control mechanism is configured to control and switch on the electromagnetic valves at the external water connection end. Water in the water body is sucked by the water pump unit into the water circulation mechanism and fed into the sealing water bladder through the water inlet end of the water circulation mechanism, and water in the sealing water bladder is discharged from the water circulation mechanism through the water outlet end.

As a development of the present disclosure, the sealing water bladder is connected with a plurality of groups of heat conducting fins, the plurality of groups of heat conducting fins penetrate through the groove walls of the sealing grooves. One end of each heat conducting fin is located in the electric installation cavity, and another end of the heat conducting fin is located in the sealing water bladder.

As a development of the present disclosure, at least one group of fans is arranged within the electric installation cavity.

As a development of the present disclosure, an outer temperature sensor is fixedly connected to an outer surface of the upper housing. An output end of the outer temperature sensor is connected to the input end of the control mechanism. The sealing water bladder is connected with at least one group of heating rods. One end of each heating rod is located in the electric installation cavity, and another end of the heating rod is located in the sealing water bladder.

As a development of the present disclosure, a pressing groove is provided in the upper surface of the lower housing, at a position close to an outer edge of the lower housing. The pressing groove is located outside the sealing groove. A pressing block is fixedly connected to the lower surface of the upper housing, at a position close to an outer edge of the upper housing, the pressing block is inserted into the pressing groove.

As a development of the present disclosure, contact surfaces between the pressing block and the pressing groove are provided with glue layers.

As a development of the present disclosure, screw holes are opened in the pressing groove, screws are connected to the lower surface of the upper housing, and the screws and the screw holes are connected to each other.

The beneficial effects of the present disclosure are provided as follows. For the present disclosure, the sealing grooves are provided respectively on the upper surface of the lower housing and the lower surface of the upper housing, and the sealing water bladder is arranged within the sealing grooves, the sealing performance of the upper and lower housings after the upper and lower housings are tightly assembled is improved by expansion of the sealing water bladder filled with water. The inner temperature sensor is arranged within the housing body. The inner temperature sensor is configured to sense a temperature within the housing body. When a heat dissipation treatment is required to be carried out within the housing body, the water circulation mechanism is activated, so that water in the sealing bladder is communicated with water in the water body, and the water is circulated between the sealing water bladder and the water body, thereby facilitating the cooling of the monitoring device. The outer temperature sensor is arranged outside the housing body. When an external environment is bad or a temperature of the water body is low, in order to ensure a normal operation of the electrical components within the housing body, the air within the housing body is heated by the at least one group of heating rods, and the liquid within the sealing water bladder can also be heated by the at least one group of heating rods. At this time, the sealing water bladder has a function of thermal insulation, which facilitates the warming of the housing body. The monitoring device has a simple structure and high sealing performance, and it is easy to operate and flexible to use. Furthermore, it is conducive to temperature adjustment within the monitoring device, and it is also easy to promote and popularize.

LIST OF REFERENCE NUMERALS

1 housing body; 2 lower housing; 3 upper housing; 4 pressing block; 5 sealing groove; 6 sealing water bladder; 7 water pipe; 8 water tank; 9 screw hole; 10 pressing groove; 11 screw; 12 heat conducting pin; 13 electric installation cavity; 14 monitoring probe; 15 fan; 16 outer temperature sensor; 17 inner temperature sensor; 18 filter; 19 control mechanism; 20 communication mechanism; 21 sensor; 22 power box; 23 water pump unit; 24 electromagnetic valve.

DETAILED DESCRIPTION

The present application is described in further detail below in conjunction with the accompanying drawings. It is necessary to point out that the following specific implementations are only used to further illustrate the application and cannot be construed as limiting the scope of protection of the application. Those skilled in the art can make some non-essential improvements and adjustments to this application, based on the contents mentioned above.

Embodiment 1

Figure 1:
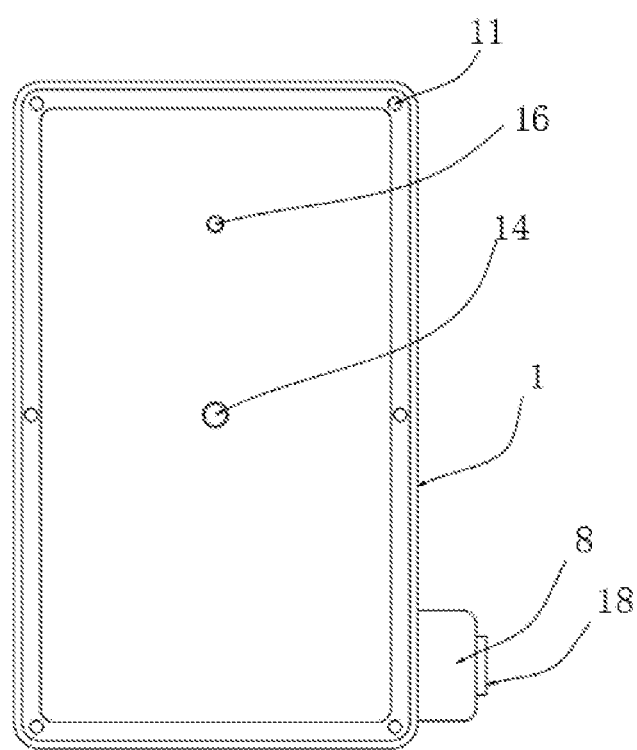
FIG. 1 is a schematic diagram of an overall structure according to the present disclosure.
Figure 2:
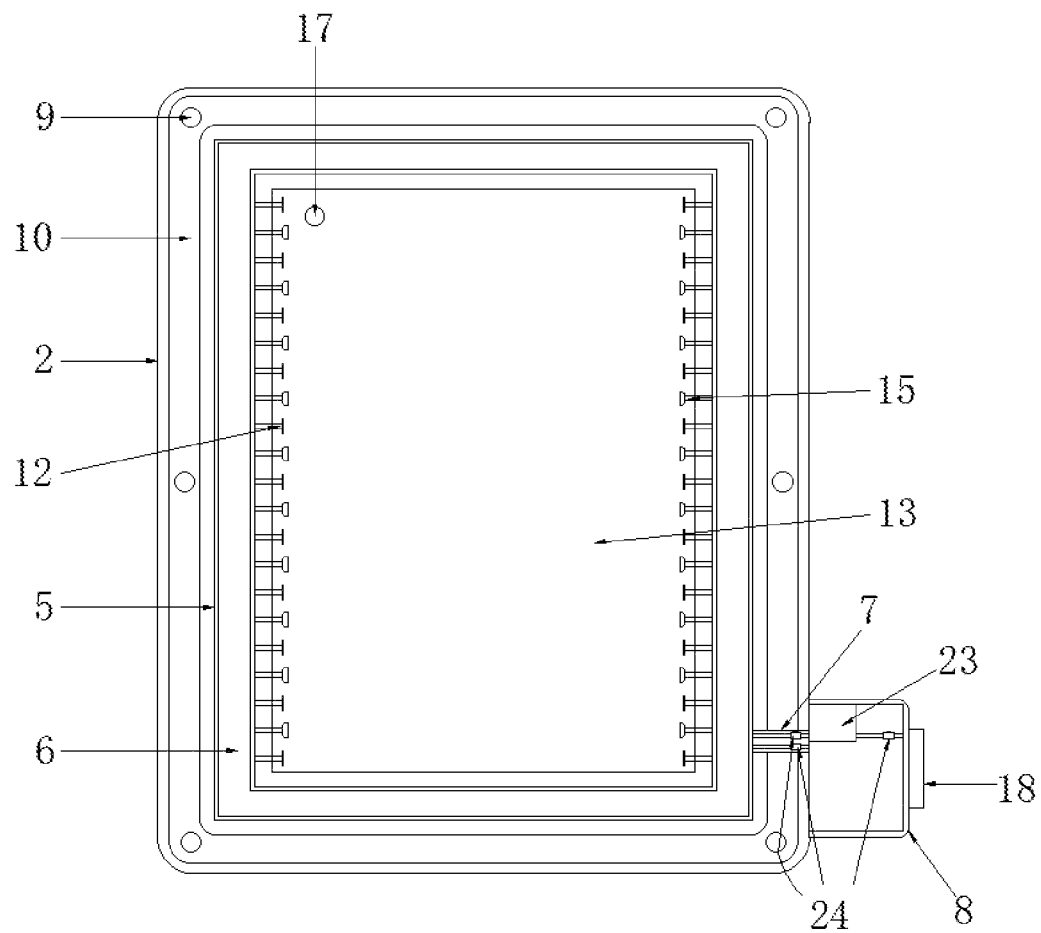
FIG. 2 is a schematic diagram of an internal structure of a lower housing according to the present disclosure.
Figure 3:
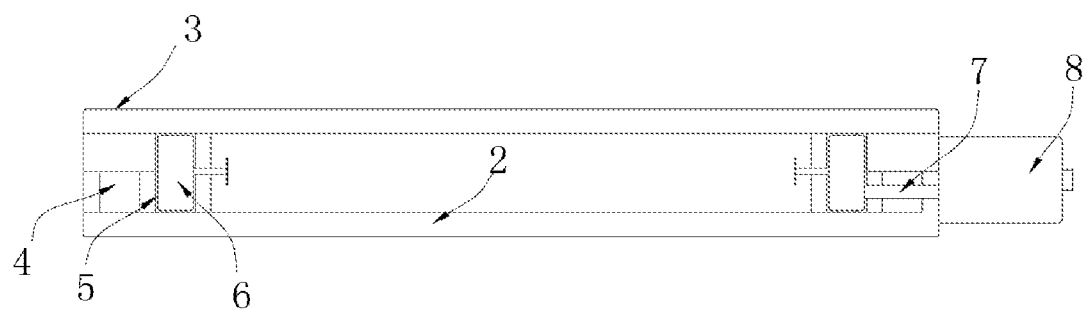
FIG. 3 is a schematic side view of the overall structure shown in FIG. 1 according to the present disclosure.
Figure 4:
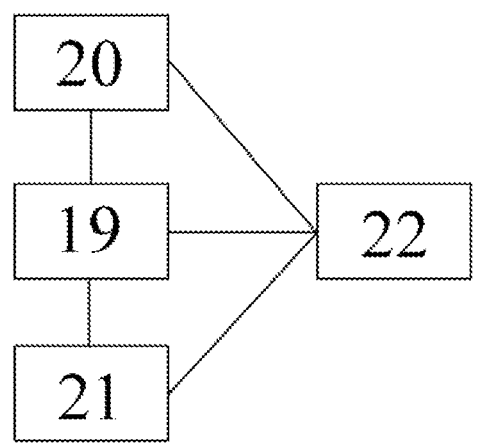
FIG. 4 is a schematic structural diagram of components arranged within a housing body according to the present disclosure.

As shown in FIGS. 1-4, it is provided a transboundary-area water-body monitoring and early warning system, including a monitoring device placed in water body to monitor the water body. The monitoring device includes a housing body 1. A control mechanism 19, a communication mechanism 20, a sensor 21 and a power box 22 are provided within the housing body 1, as shown in FIG. 4. A power end of the control mechanism 19, a power end of the sensor 21 and a power end of the communication mechanism 20 are electrically connected to an output end of the power box 22. A control terminal of the communication mechanism 20, a control terminal of the sensor 21 both are electrically connected to a control terminal of the control mechanism 19. The control mechanism 19 is configured to receive a signal sent by the sensor 21, and then send the signal from the sensor 21 to a background computer through the communication mechanism 20. The housing body 1 includes a lower housing 2 and an upper housing 3. The lower housing 2 are sealably connected to the upper housing 3. An electric installation cavity 13 is provided between the upper housing 3 and the lower housing 2. The control mechanism 19, the communication mechanism 20, the sensor 21 and the power box 22 are installed within the electric installation cavity 13. A monitoring probe 14 is vertically installed in a middle of the upper housing 3. The monitoring probe 14 is connected to the sensor 21. Sealing grooves 5 are provided respectively on an upper surface of the lower housing 2 and a lower surface of the upper housing 3, at a position close to inner side surfaces of the lower housing 2 and the upper housing 3. When the upper housing 3 and the lower housing 2 are assembled, the sealing groove 5 of the upper housing and the sealing groove 5 of the lower housing are matched with each other. A sealing water bladder 6 is arranged within the sealing groove 5 of the low housing or the sealing groove 5 of the upper housing. The housing body 1 is provided with a water circulation mechanism. The water circulation mechanism includes a water inlet end, a water outlet end and an external water connection end. The water inlet end and the water outlet end of the water circulation mechanism are connected to the sealing water bladder 6. The external water connection end is communicated with an external environment. The control terminal of the control mechanism 19 is connected to a control terminal of the water circulation mechanism. The control mechanism 19 is configured to control the water circulation mechanism to fill the sealing water bladder 6 with liquid. The sealing water bladder 6 is expanded so as to be in close contact with groove walls of the sealing grooves 5.

The control mechanism 19 may be a single chip controller, and the communication mechanism 20 may be a communication module which is generally used in Internet of Things. The sealing grooves 5 are provided respectively in the upper surface of the lower housing and the lower surface of the upper housing. The sealing water bladder 6 is arranged within the sealing grooves 5. Sealing performance of the upper and lower housings after they are tightly assembled is improved by expansion of the sealing water bladder 6 filled with water. In this embodiment, a lower surface of the sealing water bladder 6 is fixedly connected to a bottom of the sealing groove 5 of the lower housing 2, the fixed connection between the sealing water bladder and the sealing groove may be in an adhesive manner. An upper surface of the sealing water bladder 6 is provided with a first strip-typed magnet, and a second strip-typed magnet matched with the first strip-typed magnet is arranged at a bottom (when assembled, it becomes a top of the assembled sealing groove) of the sealing groove 5 of the upper housing 3. The sealing water bladder 6 is expanded by filling with water, and then the first strip-typed magnet and the second strip-typed magnet attract and fix with each other, which further improves sealing effect of the sealing water bladder 6 and reduces dynamic impact on the sealing water bladder 6 during an operation of the water circulation mechanism.

The water circulation mechanism includes a water pump unit 23 and three groups of electromagnetic valves 24. The water pump unit 23 may be an underwater water pump. The three groups of electromagnetic valves 24 may be respectively arranged at a water inlet end, a water outlet end, and an external water connection end of the water circulation mechanism. In an initial state, the electromagnetic valves 24 of the water circulation mechanism at the external water connection end and the water inlet end may be first switched on, and the water from the water body may be injected into the sealing water bladder 6, so that the sealing water bladder 6 may be expanded to be in close contact with groove walls of the sealing grooves 5. The water circulation mechanism may include a water tank 8. The external water connection end may be located on an outer surface of the water tank 8. The outer surface of the water tank 8 is fixedly connected with a filter 18 which may be fine filter net. In the practice, the outer surface of the water tank 8 may be generally connected with a water pipe 7 as a main pipe. The water pipe 7 may be communicated with the sealing water bladder 6. Two thin pipes may be provided within the water pipe 7 and be respectively the water inlet end and the water outlet end of the water circulation mechanism. The water pump unit 23 may be provided within the water tank 8. An inner temperature sensor 17 may be fixedly connected to an interior of the housing body 1 and an output end of the inner temperature sensor 17 may be electrically connected to an input end of the control mechanism 19. When a temperature valve sensed by the inner temperature sensor 17 is greater than a predetermined value, the control mechanism 19 may be configured to control to switch on the electromagnetic valves 24 at the external water connection end, and the water pump unit 23 works to introduce the water in the water body into the water circulation mechanism, so that the water in the water body enters into the sealing water bladder 6 through the water inlet end of the water circulation mechanism, and the water in the sealing water bladder 6 is discharged from the water circulation mechanism through the water outlet end. A temperature within the housing body 1 may be sensed by the inner temperature sensor 17. When a heat dissipation treatment is required to be carried out within the housing body 1, the water circulation mechanism is activated, so that the water in the sealing water bladder 6 is communicated with the water in the external water body and the water is circulated between the sealing water bladder and the external water body, thereby facilitating the cooling of the monitoring device. The sealing water bladder 6 may be connected with a plurality of groups of heat conducting fins 12, and the heat conducting fins 12 may penetrate through the groove walls of the sealing grooves 5. One end of each heat conducting fin 12 may be located in the electrical installation cavity 13 and the other end thereof may be located in the sealing water bladder 6. The heat conducting fin 12 facilitates the conduction of heat into the sealing water bladder 6. At least one group of fans 15 may be provided within the electric installation cavity 13, the at least one group of fans 15 may assist air circulation in the housing, thereby facilitating heat absorption of the heat conducting fins 12 and heating of the heating rods. An outer surface of the upper housing 3 may be fixedly connected with an outer temperature sensor 16. An output end of the outer temperature sensor 16 may be connected to an input end of the control mechanism 19. The sealing water bladder 6 may be connected with at least one group of heating rods. Each heating rod has one end located within the electric installation cavity 13 and the other end located within the sealing water bladder 6. When an external environment is bad or a temperature of the water body is low, in order to ensure a normal operation of the electrical components in the housing body 1, the heating rod may be activated. A control terminal of the heating rod is also connected to the control mechanism 19. By the heating of the heating rods, air in the housing body 1 is heated, and liquid in the sealing water bladder 6 is also heated. At this time, the sealing water bladder 6 has a function of thermal insulation, thereby facilitating the warming of the housing body 1. A pressing groove is provided in the upper surface of the lower housing 2, at a position close to the outer side surface of the lower housing 2. The pressing groove 10 is located outside the sealing groove 5. A pressing block 4 is fixedly connected to the lower surface of the upper housing 3, at a position close to the outer side surface of the upper housing 3. The pressing block 4 is inserted into the pressing groove 10. Contact surfaces between the pressing block 4 and the pressing groove 10 are provided with glue layers, so as to improve waterproofness of the monitoring device. Screw holes 9 may be formed in the pressing groove 10. Screws 11 are connected to the lower surface of the upper housing 3, and the screws 11 and the screw holes 9 are connected to each other in a mating manner. The screws 11 and the screw holes 9 may connect the upper housing 3 and the low housing 2 more tightly.

For the transboundary-area water-body monitoring and early warning system of the present disclosure, when used, the sealing grooves 5 are provided respectively on the upper surface of the lower housing and the lower surface of the upper housing. The sealing water bladder 6 is arranged within the sealing groove 5, sealing performance of the upper and lower housings after the upper and lower housings are tightly installed is improved by expansion of the sealing water bladder filled with water. The inner temperature sensor 17 is installed within the housing body 1. The inner temperature sensor 17 is configured to sense a temperature within the housing body 1. When a heat dissipation treatment is required to be carried out within the housing body 1, the water circulation mechanism is activated, so that water in the sealing bladder 6 is communicated with water in the water body, and the water is circulated between the sealing water bladder 6 and the water body, thereby facilitating the cooling of the monitoring device. The outer temperature sensor 16 is arranged outside the housing body 1. When an external environment is bad or a temperature of the water body is low, in order to ensure a normal operation of the electrical components within the housing body 1, the air within the housing body 1 is heated by the heating rods, and the liquids within the sealing water bladder 6 can be heated. At this time, the sealing water bladder 6 has a function of thermal insulation, which facilitates the warming of the housing body 1. The monitoring device has a simple structure and high sealing performance, and it is easy to operate and flexible to use. Furthermore, it is conducive to temperature adjustment within the monitoring device, and it is easy to promote and popularize.

The above mentioned embodiments only show several implementation modes of the present disclosure, and the description is relatively specific and detailed, but it should not be understood as a limitation to the protection scope of the present disclosure. It should be pointed out that for those of ordinary skill in the art, without departing from the concept of the present disclosure, several modifications and improvements can be made, and these all fall within the protection scope of the present disclosure.

What is claimed is:

1. A transboundary-area water-body monitoring and early warning system, comprising:
    a monitoring device placed in water body to monitor the water body, wherein the monitoring device comprises a housing body in which a control mechanism, a communication mechanism, a sensor and a power box are arranged;
    power ends of the control mechanism, the sensor, and the communication mechanism are electrically connected to an output end of the power box;
    control ends of the communication mechanism and the sensor are electrically connected to a control end of the control mechanism;
    the control mechanism is configured to receive a signal sent by the sensor, and send the signal from the sensor to a background computer through the communication mechanism;
    the housing body comprises a lower housing and an upper housing which are hermetically connected and define an electric installation cavity there between;
    the control mechanism, the communication mechanism, the sensor and the power box are installed within the electric installation cavity;
    a monitoring probe is installed vertically in a middle of the upper housing and is connected with the sensor, sealing grooves are provided in an upper surface of the lower housing and a lower surface of the upper housing, at positions close to outer edges of the lower housing and the upper housing, respectively;
    when the upper housing and the lower housing are assembled, the sealing grooves are arranged facing each other and a sealing water bladder is arranged within the sealing grooves;
    the housing body is provided with a water circulation mechanism, which comprises a water inlet end, a water outlet end and an external water connection end;
    the water inlet end and the water outlet end of the water circulation mechanism are connected to the sealing water bladder, the external water connection end is in communication with outside of the housing body;
    the control end of the control mechanism is connected to a control end of the water circulation mechanism;
    the control mechanism is configured to control the water circulation mechanism to fill the sealing water bladder with liquid, the sealing water bladder is expanded so as to come into close contact with groove walls of the sealing grooves;
    the water circulation mechanism comprises a water pump unit and three groups of electromagnetic valves; wherein the three groups of electromagnetic valves are respectively arranged at the water inlet end, the water outlet end, and the external water connection end of the water circulation mechanism; and in an initial state, the electromagnetic valves of the water circulation mechanism at the external water connection end and the water inlet end are first switched on, and water in the water body is injected into the sealing water bladder, so that the sealing water bladder is expanded to come into close contact with the groove walls of the sealing grooves;
    the water circulation mechanism comprises a water tank, wherein the external water connection end is located on an outer surface of the water tank, and a filter is fixedly connected to the outer surface of the water tank; and
    an inner temperature sensor is fixedly connected to an interior of the housing body, an output end of the inner temperature sensor is electrically connected to an input end of the control mechanism, when a temperature value sensed by the inner temperature sensor is greater than a predetermined value, the control mechanism is configured to control and switch on the electromagnetic valves at the external water connection end.

2. The transboundary-area water-body monitoring and early warning system according to claim 1, wherein
    water in the water body is sucked by the water pump unit into the water circulation mechanism and fed into the sealing water bladder through the water inlet end of the water circulation mechanism, and water in the sealing water bladder is discharged from the water circulation mechanism through the water outlet end.

3. The transboundary-area water-body monitoring and early warning system according to claim 2, wherein the sealing water bladder is connected with a plurality of groups of heat conducting fins, the plurality of groups of heat conducting fins penetrate through the groove walls of the sealing grooves; and
    one end of each heat conducting fin is located in the electric installation cavity, and another end of the heat conducting fin is located in the sealing water bladder.

4. The transboundary-area water-body monitoring and early warning system according to claim 3, wherein at least one group of fans is arranged within the electric installation cavity.

5. The transboundary-area water-body monitoring and early warning system according to claim 4, wherein an outer temperature sensor is fixedly connected to an outer surface of the upper housing;

an output end of the outer temperature sensor is connected to the input end of the control mechanism; the sealing water bladder is connected with at least one group of heating rods; and one end of each heating rod is located in the electric installation cavity, and another end of the heating rod is located in the sealing water bladder.

6. The transboundary-area water-body monitoring and early warning system according to claim 1, wherein a pressing groove is provided in the upper surface of the lower housing, at a position close to an outer edge of the lower housing; the pressing groove is located outside the sealing groove; and a pressing block is fixedly connected to the lower surface of the upper housing, at a position close to an outer edge of the upper housing, the pressing block is inserted into the pressing groove.

7. The transboundary-area water-body monitoring and early warning system according to claim 6, wherein contact surfaces between the pressing block and the pressing groove are provided with glue layers.

8. The transboundary-area water-body monitoring and early warning system according to claim 7, wherein screw holes are opened in the pressing groove, screws are connected to the lower surface of the upper housing, and the screws and the screw holes are connected to each other.

* * * * *